United States Patent
Nagarajan

(10) Patent No.: US 9,907,469 B2
(45) Date of Patent: Mar. 6, 2018

(54) COMBINING INFORMATION FROM MULTIPLE FORMATS

(71) Applicant: Google Inc., Mountain View, CA (US)

(72) Inventor: Guru Nagarajan, San Jose, CA (US)

(73) Assignee: Google LLC, Mountain View, CA (US)

( * ) Notice: Subject to any disclaimer, the term of this patent is extended or adjusted under 35 U.S.C. 154(b) by 234 days.

(21) Appl. No.: 14/158,640

(22) Filed: Jan. 17, 2014

(65) Prior Publication Data

US 2015/0164435 A1    Jun. 18, 2015

Related U.S. Application Data

(60) Provisional application No. 61/915,458, filed on Dec. 12, 2013.

(51) Int. Cl.
| | | |
|---|---|---|
| A61B 5/00 | (2006.01) | |
| A61B 5/0205 | (2006.01) | |
| A61B 5/024 | (2006.01) | |
| G06F 19/00 | (2018.01) | |

(52) U.S. Cl.
CPC .......... *A61B 5/0015* (2013.01); *A61B 5/0002* (2013.01); *A61B 5/024* (2013.01); *A61B 5/0205* (2013.01); *G06F 19/322* (2013.01); *G06F 19/3443* (2013.01)

(58) Field of Classification Search
CPC .................................. A61B 5/02; A61B 5/00
USPC ........................................................ 600/300
See application file for complete search history.

(56) References Cited

U.S. PATENT DOCUMENTS

| | | |
|---|---|---|
| 6,440,068 B1 | 8/2002 | Brown et al. |
| 7,039,878 B2 | 5/2006 | Auer et al. |
| 2004/0034289 A1 | 2/2004 | Teller et al. |
| 2007/0135855 A1 | 6/2007 | Foshee et al. |
| 2012/0143093 A1 | 6/2012 | Stirling et al. |
| 2012/0177256 A1 | 7/2012 | Keefe et al. |
| 2013/0304510 A1 | 11/2013 | Chen et al. |
| 2013/0304512 A1 | 11/2013 | Seshadri et al. |

FOREIGN PATENT DOCUMENTS

JP    2013-242745 A    12/2013

OTHER PUBLICATIONS

Extended European Search Report from European Patent Application No. 14868899.7, dated Nov. 14, 2017, 8 pages.

*Primary Examiner* — Carl H Layno
*Assistant Examiner* — Jon Eric C Morales
(74) *Attorney, Agent, or Firm* — McDermott Will & Emery LLP

(57) ABSTRACT

Techniques for combining physiological and health information are provided. An example method includes receiving one or more physiological parameters of a user from one or more devices in data formats specific to the devices, translating the received physiological parameters from their respective data formats into a common data format, storing the translated physiological parameters into a common data structure configured to store data in the common data format, retrieving the stored physiological parameters for display in a user interface, wherein the user interface displays one or more human-readable physiological characteristics of the user based on the retrieved physiological parameters, and repeating the translating, the storing and the retrieving, upon receipt of one or more other physiological parameters from the devices, to update the displayed human-readable physiological characteristics.

20 Claims, 5 Drawing Sheets

COMBINING INFORMATION FROM MULTIPLE FORMATS

RELATED APPLICATIONS

This application is a non-provisional of U.S. Provisional Patent Application No. 61/915,458, filed on Dec. 12, 2013 and titled "Combining Information From Multiple Formats", which is herein incorporated in its entirety by reference.

BACKGROUND

The present disclosure generally relates to physiological and health information. Users are increasingly using digital monitoring devices or sensors to obtain personal physiological or health-related parameters. For example, a user may wear a temperature sensor on the user's wrist that may display the user's body temperature. The user may also wear a heart rate sensor on the user's chest that may monitor the user's heart rate.

SUMMARY

The disclosed subject matter relates to combining physiological and health information.

In one innovative aspect, the disclosed subject matter can be embodied in a method. The method comprises receiving one or more physiological parameters of a user from one or more devices in data formats specific to the devices, translating the received physiological parameters from their respective data formats into a common data format, storing the translated physiological parameters into a common data structure configured to store data in the common data format, retrieving the stored physiological parameters for display in a user interface, wherein the user interface displays one or more human-readable physiological characteristics of the user based on the retrieved physiological parameters, and repeating the translating, the storing and the retrieving, upon receipt of one or more other physiological parameters from the devices, to update the displayed human-readable physiological characteristics.

In this way, the user may conveniently view human-readable physiological characteristics from different devices via a common user interface on the user's device even when the devices provide physiological parameters in data formats specific to the devices. This saves the user time and helps the user more easily gain insight into the user's health.

In another innovative aspect, the disclosed subject matter can be embodied in a method. The method comprises receiving one or more physiological parameters of a user from one or more devices in data formats specific to the devices, translating the received physiological parameters from their respective data formats into a common data format, storing the translated physiological parameters in the common data format at a server, and instructing the server to permit one or more applications to retrieve the stored physiological parameters, wherein the permitted applications display one or more physiological characteristics of the user based on the retrieved physiological parameters.

In this way, a user may permit third-party applications to retrieve the user's physiological parameters and display physiological characteristics and other information associated with the user's health based on the user's physiological parameters. This benefits the user because the user can make available the user's physiological parameters to numerous third-party applications that can provide useful health-related information to the user based on the physiological parameters.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

DETAILED DESCRIPTION

Figure 1:
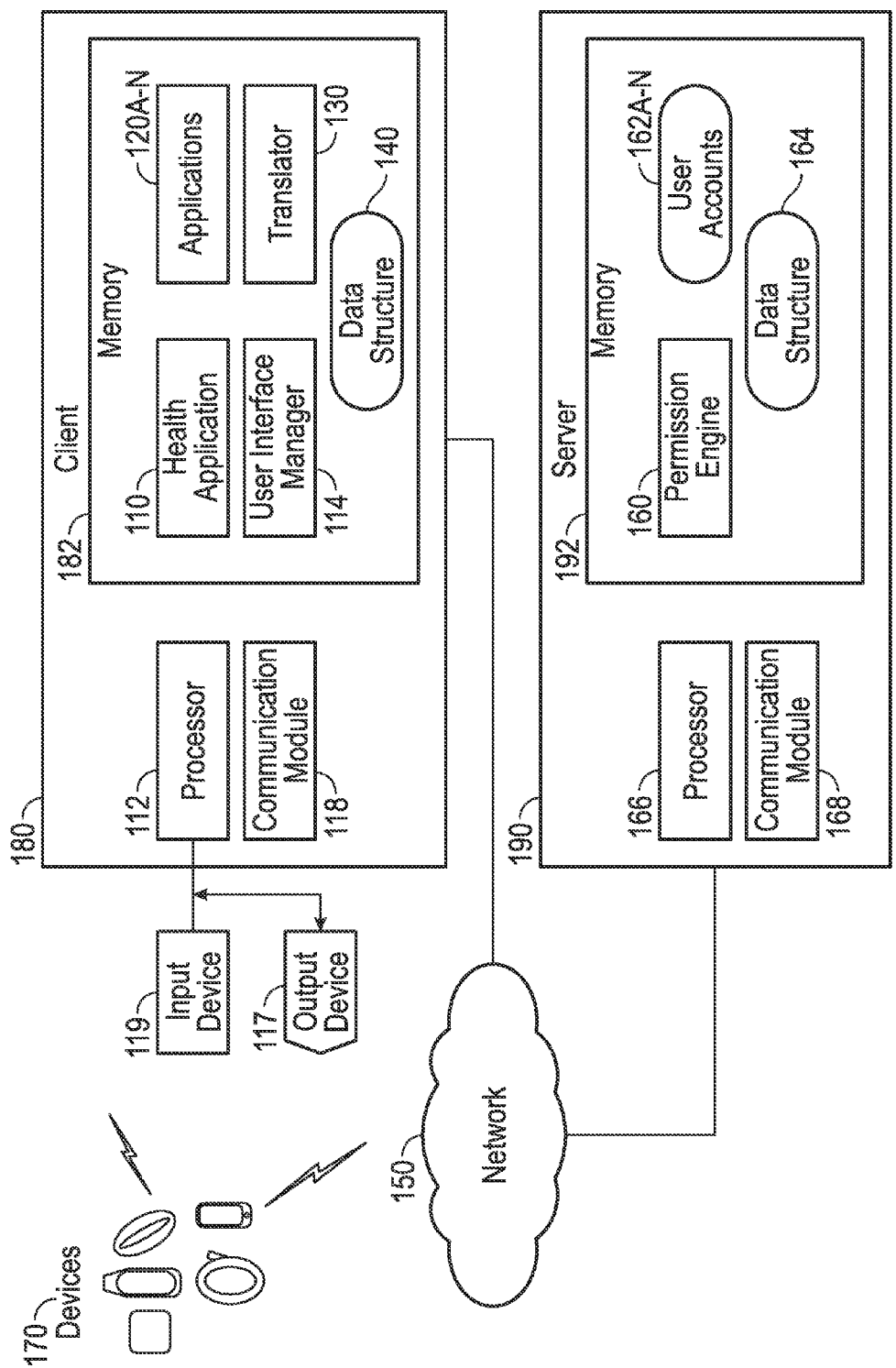
FIG. 1 is a diagram of an example network environment suitable for practicing an implementation of the subject technology.

The detailed description set forth below is intended as a description of various configurations of the subject technology and is not intended to represent the only configurations in which the subject technology may be practiced. The appended drawings are incorporated herein and constitute a part of the detailed description. The subject technology is not limited to the specific details set forth herein and may be practiced without these specific details.

The disclosed subject matter relates to combining physiological and health information.

In some implementations, one or more physiological parameters (e.g., blood pressure, body temperature, weight, etc.) of a user can be received from one or more devices (e.g., physiological sensors) worn by the user or in proximity to the user. The devices may be manufactured by the same or different manufacturers and may provide physiological parameters of the user in formats specific to the devices. For example, a heart sensor may provide heart rate parameters in a first data format and a body temperature sensor may provide body temperature parameters in a second data format distinct from the first data format. The devices and sensors disclosed herein are not limited to physiological and health sensors and can work with any other devices (e.g., any mobile device sensor) other than physiological and health sensors.

In some implementations, the physiological parameters received from the one or more devices in data formats specific to the devices may be translated from their respective data formats into a common data format. The common data format may be distinct from the respective data formats. The translated physiological parameters may then be stored in a common data structure configured to store data in the common data format. The data structure may be a local data structure resident at a client device or a remote data structure resident at a remote server. In this way, information from different devices in multiple formats may be combined into a common data format for storage or transmission.

The stored physiological parameters may be retrieved for display in a user interface. The user interface may be a user interface of the user's mobile device. The user interface may display one or more human-readable physiological characteristics of the user based on the retrieved physiological parameters. The human-readable physiological characteristics may include physiological parameter values, graphs, imagery, and video/animation(s) that may relate to the user's health. In some implementations, the translation, the storing and the retrieving of the physiological parameters, may be repeated, upon receipt of one or more other physiological parameters from the devices, to update the displayed human-readable physiological characteristics.

In this way, the user can conveniently view human-readable physiological characteristics (and any other health-related data) from the different devices via a common interface on the user's device. The user need not open separate applications to view physiological parameters from different physiological sensors or devices. This saves the user time and helps the user more easily gain insight into the user's health.

In some implementations, the translated physiological parameters may be stored in the common data format in a data structure at a remote server. The server may be instructed to permit one or more applications to retrieve the stored physiological parameters. The permitted applications may be third-party applications that may be configured to receive and display the physiological parameters or physiological characteristics based on the physiological parameters. In some implementations, the server may be instructed to permit the one or more applications to retrieve the stored physiological parameters based on an indication from a user. For example, the indication from the user may include a selection of user interface elements representing the one or more applications. When the user opens or executes the permitted applications, the permitted applications may display one or more physiological characteristics of the user based on the retrieved physiological parameters.

In this way, a user may permit third-party applications to retrieve the user's physiological parameters and display physiological characteristics and other information associated with the user's health based on the user's physiological parameters. This benefits the user because the user need not rely on a limited number of applications specific to the devices capturing the physiological parameters, but instead can make available the user's physiological parameters to numerous third-party applications that can provide useful health-related information to the user based on the physiological parameters.

It is to be appreciated that the devices and sensors disclosed herein are not limited to physiological and health sensors and can work with any other devices (e.g., any mobile device sensor, transmitter, receiver, etc.) other than physiological and health sensors. Furthermore, the disclosed implementations are not limited to health and physiological information and can combine other types of data in multiple formats into a common data format. Such data can include, but is not limited to audio data, video data, imaging data, geographic data and any combination thereof having any data format or file type. Furthermore the sensors or devices, can include, but are not limited to, audio devices, pressure devices, fingerprint devices, biometric devices, temperature sensors, light sensors, barometric sensors, barometric sensors or any combination thereof. As a purely illustrative and non-limiting example, the disclosed implementations may combine data in a first format from a temperature sensor with barometric data in a second format from a pressure sensor into a common data format for combined storage or transmission in the common data format.

FIG. 1 illustrates example architecture 100 for providing physiological and health-related information to a user. Architecture 100 includes devices 170, client 180 and server 190 connected over network 150.

Devices 170 can include physiological sensors or devices configured to measure and monitor physiological parameters. For example, devices 170 can include heart-rate sensors, temperature sensors, pedometers, etc. Devices 170 can also include mobile devices, such as smartphones, configured to monitor physiological parameters. In some aspects, devices 170 may monitor environmental parameters in proximity to a user such as temperature, humidity, etc. Devices 170 may communicate over communication protocols, such as Bluetooth or WiFi, to provide the physiological parameters to client 180 and server 190. Devices 170 may provide physiological parameters and related data in formats specific to the devices. For example, a heart sensor may provide heart rate parameters in a first data format and a body temperature sensor may provide temperature parameters in a second data format distinct from the first data format. Devices 170 may be manufactured by the same or different manufacturers.

Client 180 can be, for example, a desktop computer, laptop computer, mobile device (e.g., a smartphone, tablet computer, or PDA), set top box (e.g., for a television), video game console, or any other device having appropriate processor, memory, and communications capability. Client 180 is configured to execute applications that can be, for example, health-related applications, search applications, web browsers, reading applications, communication applications, or any other software application.

Client 180 includes processor 112, communication module 118 and memory 182. Memory 182 can include health application 110, applications 120A-N, translator 130, data structure 140, and user interface manager 114. Output device 117 can include a touch screen display or any other graphic display. Client 180 also includes input device 119, such as a keyboard, touchscreen, or mouse, to receive user input. Processor 112 of client 180 can be configured to execute instructions, such as instructions physically coded into processor 112 and instructions received from software (e.g., health application 110 and translator 130) in memory 182. For example, processor 112 of client 180 may execute instructions from translator 130 to translate physiological parameters received from devices 170 into a common data format. Client 180 can further include health application 110, applications 120A-N, translator 130, data structure 140 and user interface manager 114.

In some implementations, health application 110 may be a mobile device application (or "app") resident on client 180 which may be a mobile device. Health application 110 can be configured to run on client 180 that may be mobile or non-mobile. Health application 110 may be an application focused on user-health or well-being or can be any other application (e.g., browser, reader, etc.) that may display information from data structure 140. Applications 120A-N may be third-party applications that may be permitted by the user to access the user's physiological parameters and health related data from data structures 140 or 164. Translator 130 may be configured to translate one or one or more physiological parameters of a user received from devices 170 for storage in a common data format at data structures 140 and 164. User interface manager 114 may retrieve the translated physiological parameters and other health-related data from data structures 140 and 164 for display on a user interface of health application 110.

In some implementations, translator 130 receives one or one or more physiological parameters (e.g., blood pressure, body temperature, weight, etc.) of a user from devices 170 (e.g., physiological sensors) worn by the user or in proximity to the user. As noted above, devices 170 may be manufactured by the same or different manufacturers and may provide physiological parameters of the user in formats and application program interfaces (APIs) specific to the devices. For example, a heart sensor may provide heart rate parameters in a first data format and a body temperature sensor may provide temperature parameters in a second data format distinct from the first data format. In situations in which the systems discussed here collect physiological information about users, or may make use of physiological information, the users may be provided with an opportunity to control whether programs or features collect or share user information (e.g., information about a user's physiological parameters, a user's preferences, etc.). Thus, the user may have control over how information is collected about the user and used by a server.

The physiological parameters received from the one or more devices in data formats specific to the devices may be translated by translator 130 from their respective data formats into a common data format. The common data format may be distinct from the respective data formats. In some implementations the common data format may be defined using a mark-up language. The mark-up language may include tags or identifiers to describe a type of physiological parameter, an identifier identifying a device of devices 170 that captured or measured the parameter and a date or time at which the parameter was captured or measured. The markup language may include markup symbols to describe the contents of a common data format file including physiological parameters and other health-related data. The markup language may describe the contents in terms of what data is being described. For example, the word "bodytemp" placed within markup tags could indicate that the data that follows is a body temperature value. In another example, the word "timestamp" placed within markup tags could indicate that the data that follows is a time at which a physiological parameter was captured by one or more devices 170.

In some implementations, the physiological parameters translated by translator 130 may be stored in data structure 140. Data structure 140 can be included in any database in memory 182. Data structure 140 can, for example, include a file formatted in the common data format. For example, a portion of the file may include a tag identifying the type of parameter (e.g., blood glucose, heart-rate, etc.), followed by a value (or magnitude) of the parameter, a tag identifying a time at which the parameter was measured by a device and a tag identifying the name or identifier (e.g., serial number) of the device. The file may include hundreds, thousands or any other number of parameters stored in the common data format. In some implementations, the file (or any other data structure) may be updated and kept current with latest values of parameters received from devices 170. The data stored in data structure 140 may be transmitted by health application 110 to a remote data structure 164 at server 190. Data structure 164 may reside, for example, in a database in memory 192.

In some implementations, health application 110 may synchronize or (or "sync") the data stored at data structure 164 with data stored at data structure 140. In this way, a user may be able to access the user's physiological and health-related data even when the user is offline and disconnected from server 190. Furthermore, because the data is stored at remote data structure 164, the user may be able to access the data at data structure 164 from any other client device separate from client 180.

In this way, because physiological parameters received from devices 170 have been translated into a common data format by translator 130, data structure 140 and data structure 164 may store physiological parameters in a common data format even if devices 170 provide the parameters in their respective specific (e.g., proprietary) data formats.

In some implementations, translator 130 may translate physiological parameters received from devices 170 in real-time (or "on-the fly") as they are being received and transmit the translated parameters directly to applications 120A-N, data structure 164 or any other device on network 150 that may be configured to receive the translated parameters.

In some implementations, user interface manager 114 may retrieve one or more physiological parameters and related data from data structure 140 and display the parameters in the user interface of health application 110. In some implementations, the user interface manager 114 may display physiological parameters from data structure 140 with consideration to the type of parameter, the time at which the parameter was measured or captured by devices 170, and a name/type of device used to measure or capture the parameter. To give such consideration, the user interface manager 114 may, for example, read a file tag identifying the type of parameter (e.g., blood glucose, heart-rate, etc.), followed by a value of the parameter, a tag identifying a time at which the parameter was measured by a device and a tag identifying the name or identifier (e.g., serial number) of the device.

The user interface manager 114 may display in the user interface of health application 110 one or more human-readable physiological characteristics of the user based physiological parameters retrieved from data structure 140. The displayed human-readable physiological characteristics may include physiological parameter values, graphs, imagery, and video/animations that can help the user gain better insight into the user's health. In some implementations, translator 130 may repeat the translation and the storing in the data structure 140 upon receipt of one or more other physiological parameters from the devices 170. The data stored in data structure 140 may be transmitted by health application 110 to a remote data structure 164 at server 190. User interface manager 114 may detect changes to data structure 140 or data structure 164 and update the displayed human-readable physiological characteristics in the user interface of health application 110 to provide real-time physiological updates to a user of health application 110.

In some implementations, the translated physiological parameters may be stored by translator 130 in the common data format at data structure 164 resident at server 190. Server 190 may be configured to store physiological parameters and other health related information in association with one or more user accounts 162A-N. For example, the physiological parameters may be stored in association with a user account 162A of the user accounts 162A-N. In some implementations, translator 130 may repeat the translation, and the storing in the data structure 164 at server 190 upon receipt of one or more other physiological parameters from the devices 170. User interface manager 114 may detect changes to data structure 164, retrieve data from data structure 164 and update the displayed human-readable physiological characteristics in the user interface of health application 110 to provide real-time physiological updates to a user of health application 110. In some implementations, data stored in data structures 140 and 164 may be used by health application 110 to display historic physiological trends to a user of health application 110.

In some implementations, translator 130 may be implemented as an application programming interface (API). The translator 130 API may be integrated into third-party physiological sensors, medical devices and software applications. In an example, such integration may be at a hardware level with changes made to one or more hardware device drivers or software interfaces to the device drivers. In some implementations, the third-party devices may be provided with a physical, touch-screen or touch sensitive button (e.g., share button). When a user selects or presses the button, translator 130 implemented on the third-party device may be instructed automatically translate the physiological parameters measured by the third-party device from their native or proprietary data format into the common data format discussed above. The translated parameters may be then transmitted for storage at data structure 164 at server 190. In this way, the user need not have immediate access to health application 110 when using a third-party device. Rather, the user may conveniently select a button on the device to upload the user's physiological parameters in the common data format to data structure 164 at server 190. As discussed above, the physiological parameters and other health related data may be retrieved by health application 110 or other third-party applications 120A-N to provide useful physiological characteristics and health-related data to the user.

In some implementations, server 190 may be instructed by health application 110 to permit the one or more applications of applications 120A-N to retrieve data from data structure 164 based on an indication from a user of health application 110. For example, the indication from the user may include a selection of user interface elements representing one or more applications 120A-N in health application 110. When the indication from the user transmitted by health application 110 and is received at server 190, permission engine 160 may store the indication (or permissions) in association with a user account 162A at server 190.

When the user opens or executes one or more applications 120A-N, the applications 120A-N may provide a request for the user's physiological parameters stored at data structure 164. Responsive to the request, permission engine 160 may check if the requesting applications have been permitted or authorized by the user's account 162A in the indication. If the requesting applications have been permitted or authorized by the user's account 162 in the indication, the requesting applications are allowed to retrieve one or more physiological characteristics of the user from data structure 164. Otherwise, permission engine 160 may not allow the requesting applications to access or read data structure 164. The permitted requesting applications may display one or more physiological characteristics of the user based on the retrieved physiological parameters. The physiological characteristics may include physiological parameter values, graphs, imagery, video/animations, and health-related suggestions to the user.

In this way, a user may permit third-party applications to retrieve the user's physiological parameters and display physiological characteristics and other information associated with the user's health based on the user's physiological parameters. This benefits the user because the user need not rely on a limited number of applications specific to the devices capturing the physiological parameters, but instead can make available the user's physiological parameters to numerous third-party applications that can provide useful health-related information to the user based on the physiological parameters.

In some implementations, server 190 may be instructed by health application 110 to permit one or more social networks (or social groups/circles) to access data structure 164 based on an indication from a user of health application 110. For example, the indication from the user may include a selection of user interface elements representing the one or more social networks in health application 110. When the indication from the user is received from health application 110 at server 190, permission engine 160 may store the indication in association with a user account 162A at server 190. When the user logs into a social network, one or more applications of the social network may provide a request for the user's physiological parameters stored at data structure 164. Responsive to the request, permission engine 160 may check if the social network (or application(s) on the social network) has been permitted or authorized via the user's account 162A in the indication. If the requesting social network has been permitted or authorized by via the user's account 162 in the indication, the requesting social network or applications of the social network are allowed to retrieve one or more physiological characteristics of the user from data structure 164. The social network may then share the user's physiological parameters with other users or applications on the social network based on the user's account settings with the social network. Otherwise, permission engine 160 may not allow the requesting social network to access data structure 164.

In this way, a user may permit various social networks, and applications configured to execute on the social networks, to retrieve the user's physiological parameters. The retrieved physiological parameters may be shared with other users for display of physiological characteristics and other information associated with the user's health based on the user's physiological parameters. The user's physiological characteristics or parameters may be up-voted, shared, liked or marked as favorite by other users in a social network.

In some implementations, server 190 may be instructed to permit the one or more user accounts 162A-N to share data based on an indication from a user of health application 110. For example, an indication from a user having a user account 162A may include a selection of user interface elements in health application 110 to share the user's physiological parameters with user accounts 162B and 162C. User accounts 162B and 162C may be accounts associated with contacts of the user. When the indication from the user is received at server 190, permission engine 160 may store the indication in association with the user account 162A at server 190. The other user accounts 162B and 162C may provide a request for the user's physiological parameters stored at data structure 164. Responsive to the request, permission engine 160 may check if user accounts 162B and 162C have been permitted or authorized via the user's account 162A in the indication. If the requesting user accounts 162B and 162C have been permitted or authorized by via the user's account 162A in the indication, the requesting user accounts 162B and 162C are allowed to retrieve one or more physiological characteristics of the user from data structure 164. The user's contacts may then be able to view the user's physiological parameters associated with user account 162A. It is to be appreciated that client 180 may also include a permission engine that may control access by applications 120A-N to data structure 140 resident on client 180.

In some implementations, a user of health application 110 may be able to initiate share the user's physiological parameters with an expert (e.g., fitness trainer, consultant etc.) during or prior to a consultation with the expert. For example, the user may determine that user account 162E belongs to a fitness trainer who the user intends to consult. The user may then provide an indication to health application 110 to permit user account 162E to access the user's physiological information and other health-related data stored in association with the user's account 162A. In some implementations, when the user provides such an indication, user account 162E belonging to the fitness trainer may receive a notification. The notification may indicate that user account 162A has shared or provided access to the user's physiological parameters. The fitness trainer may then review the physiological parameters and provide a health-related recommendation to the user that may be displayed at health application 110. In other implementations, the user may be able to have an instant messaging session, screen sharing session or even a scheduled or ad-hoc video call with the fitness trainer. The fitness trainer's account (162E) may be provided access to the user's physiological parameters prior to, during and after the call or messaging session or any other interaction mechanism.

In some implementations, correlation engine 169 at server 190 may correlate one or more physiological parameters of a user with one or more physiological characteristics and provide a result of the correlation to health application 110. The one or more physiological characteristics may be determined based on a function of physiological parameters of other users stored in association with user accounts 162A-N. For example, correlation engine 169 may determine that an average value of heart rate of user accounts 162B-N is 100 beats per minute. If the heart rate of a user of user account 162A is determined to be 80 beats per minute, correlation engine 169 may determine that the user's heart rate is lower than the average heart rate of other users 162B-N and may provide an indication to the user via the user interface of health application 110. Such an indication may include a user interface pop-up or any other user interface alteration (e.g. color change).

In some implementations, correlation engine 169 at server 190 may compare or more physiological parameters of a user with one or more physiological characteristics and of another user(s) specified by the user and provide a result of the comparison to health application 110. For example, a user having user account 162A may specify via application 110 that the user would like to compare a number of miles the user has run on a particular day with another user account 162C. The user account 162C may belong to a friend of the user. Correlation engine 169 may then read (from data structure 164) the values of miles run on the particular day associated with user accounts 162A and C and then provide the result of the comparison to health application 110. Such a result may, for example, indicate that the user account 162A has recorder a greater number of miles run on the particular day in comparison with user account 162C.

In some implementations, a user of health application 110 may be able to specify one or more users, groups of users or "contacts" with whom the user would like to automatically share one or more physiological parameters. For example, the user may specify through a user interface of health application 110 that user accounts 162B, C and D should automatically receive the user's hear rate information while user accounts 162D and F should automatically receive the user's blood glucose level information. Furthermore, the user may specify a time period for which the user intends to share the user's physiological parameters with different user accounts or groups of user accounts. For example, the user may specify via health application 110 that the user's blood glucose level should be shared with user accounts 162D and F for a period of 48 hours beginning Jan. 1, 2014. Alternatively, the user may specify that that the user's blood glucose level should be shared with user accounts 162D and F on Jan. 12, 13 and 17, 2014. These examples are purely illustrative and the user may be able to specify any other time range via a user interface of health application 110.

In some implementations, client devices separate from client 180 may access the translated physiological parameters. For example, a user may need to access the user's physiological parameters from another client (e.g., laptop) separate from client 180. For example, the user may log into the user's account 162A on the other client and request access to the user's physiological parameters. The other device may then retrieve the stored physiological parameters from data structure 164 and display them to the user in a manner similar to client 180. Similarly, other permitted users may be able to access the user's or their own respective physiological parameters stored at data structure 164 at server 190.

Server 190 can include devices having an appropriate processor, memory, and communications capability. Network 150 can include, for example, any one or more of a personal area network (PAN), a local area network (LAN), a campus area network (CAN), a metropolitan area network (MAN), a wide area network (WAN), a broadband network (BBN), the Internet, and the like. Further, network 150 can include, but is not limited to, any one or more of the following network topologies, including a bus network, a star network, a ring network, a mesh network, a star-bus network, tree or hierarchical network, and the like.

Server 190 includes processor 166, communication module 168 and memory 192. Memory 192 further includes permission engine 160, user accounts 162A-N and data structure 164. User accounts 162A-N may be associated with physiological parameters of different users. Processor 166 of server 190 can be configured to execute instructions, such as instructions physically coded into processor 166 and instructions received from software (e.g., permission engine 160) in memory 192. For example, processor 166 of server 190 may executes instructions from permission engine 160 to grant permission to one or more requesting applications 120A-N to access data structure 164.

Client 180 and server 190 are connected over network 150 via respective communications modules 118 and 168. The communications modules 118 and 168 are configured to interface with the network 150 to send and receive information, such as data, requests, responses, and commands to other devices on the network. Communications modules 118 and 168 can be, for example, modems or Ethernet cards.

Figure 2:
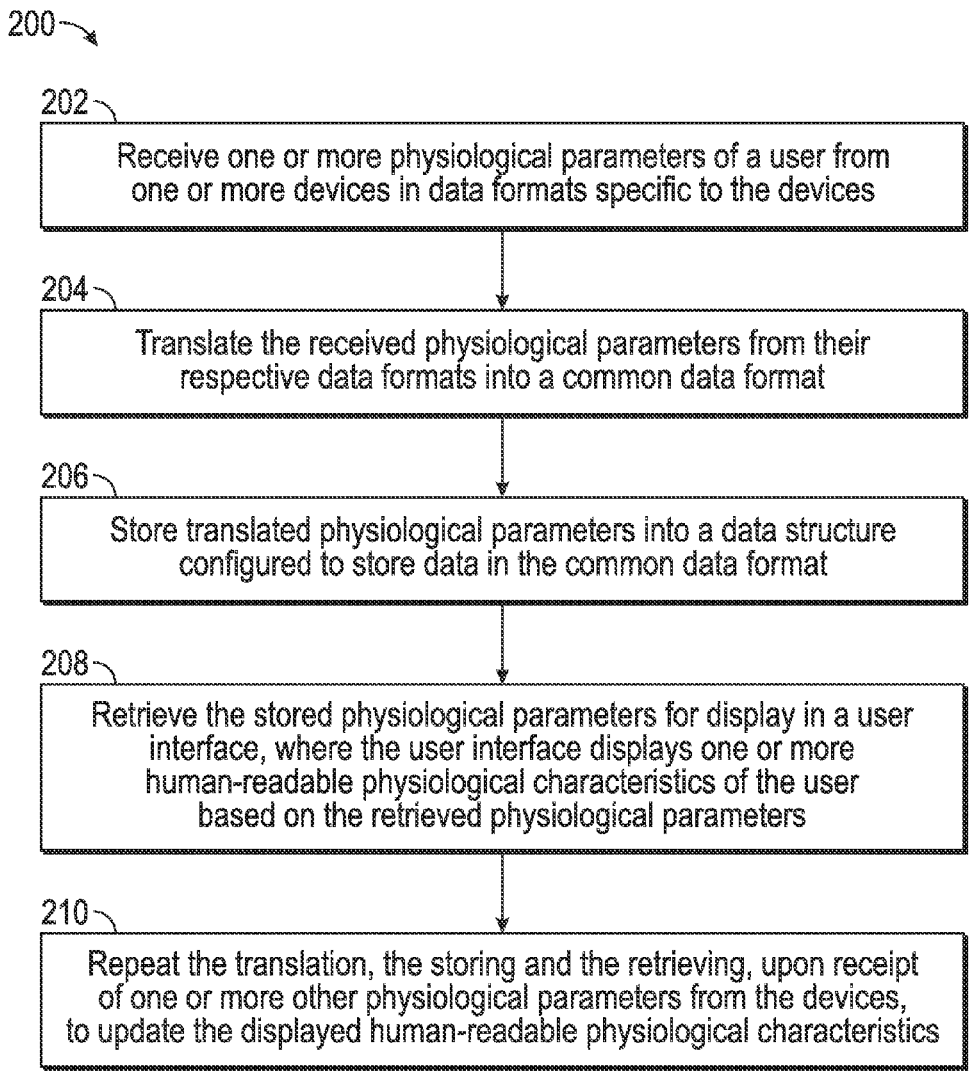
FIGS. 2 and 3 illustrate example processes for providing physiological and health information to a user.

FIG. 2 illustrates an example process 200 for providing physiological characteristics and health-related information at the example client of FIG. 1. While FIG. 2 is described with reference to FIG. 1, it should be noted that the process steps of FIG. 2 may be performed by other systems.

The process 200 begins with receiving one or more physiological parameters of a user from one or more devices in data formats specific to the devices (stage 202). As an example, translator 130 receives one or one or more physiological parameters of a user from devices 170 (e.g., physiological sensors) worn by the user or in proximity to the user. As noted above, devices 170 may be manufactured by the same or different manufacturers and may provide physiological parameters of the user in formats specific to the devices. For example, a heart sensor may provide heart rate parameters in a first data format and a body temperature sensor may provide temperature parameters in a second data format distinct from the first data format.

Process 200 proceeds by translating the received physiological parameters from their respective data formats into a common data format (stage 204). As an example, the physiological parameters received from devices 170 in data formats specific to the devices may be translated by translator 130 from their respective data formats into a common data format. The common data format may, for example, be distinct from the respective data formats. The common data format may be distinct from the respective data formats. In some implementations the common data format may be defined using a mark-up language. The mark-up language may include tags or identifiers to describe a type of physiological parameter, an identifier identifying a device of devices 170 that captured or measured the parameter and a date or time at which the parameter was captured or measured.

The translated physiological parameters are then stored into a common data structure configured to store data in the common data format (stage 206). As an example, the physiological parameters translated by translator 130 may be stored in data structure 140. Data structure 140 can, for example, include a file formatted in the common data format. For example, a portion of the file may include a tag identifying the type of parameter (e.g., blood glucose, heart-rate, etc.), followed by a value (or magnitude) of the parameter, a tag identifying a time at which the parameter was measured by a device and a tag identifying the name or identifier (e.g., serial number) of the device. The file may include hundreds, thousands or any other number of parameters stored in the common data format. In some implementations, the file (or any other data structure) may be updated and kept current with latest values of parameters received from devices 170. The data stored in data structure 140 may be transmitted by health application 110 to a remote data structure 164 at server 190.

Process 200 proceeds by retrieving the stored physiological parameters for display in a user interface, where the user interface displays one or more human-readable physiological characteristics of the user based on the retrieved physiological parameters (stage 208). As an example, user interface manager 114 may retrieve one or more physiological parameters and related data from data structure 140 and display the parameters in the user interface of health application 110.

In some implementations, the user interface manager 114 may display physiological parameters from data structure 140 with consideration to the type of parameter, the time at which the parameter was measured or captured by devices 170, and a name/type of device used to measure or capture the parameter. To give such consideration, the user interface manager 114 may, for example, read a file tag identifying the type of parameter (e.g., blood glucose, heart-rate, etc.), followed by a value of the parameter, a tag identifying a time at which the parameter was measured by a device and a tag identifying the name or identifier (e.g., serial number) of the device. User interface manager 114 may display in the user interface of health application 110 one or more human-readable physiological characteristics of the user based physiological parameters retrieved from data structure 140. The displayed human-readable physiological characteristics may include physiological parameter values, graphs, imagery, and video/animations that can help the user gain better insight into the user's health.

Process 200 may then repeat the translating (stage 204), the storing (stage 206) and the retrieving (stage 208), upon receipt of one or more other physiological parameters from the devices, to update the displayed human-readable physiological characteristics (stage 210). As an example, translator 130 may repeat the translation and the storing in the data structure 140 upon receipt of one or more other physiological parameters from the devices 170. The data stored in data structure 140 may be transmitted by health application 110 to a remote data structure 164 at server 190. User interface manager 114 may detect changes to data structure 140 or data structure 164 and update the displayed human-readable physiological characteristics in the user interface of health application 110 to provide real-time physiological updates to a user of health application 110.

Figure 3:
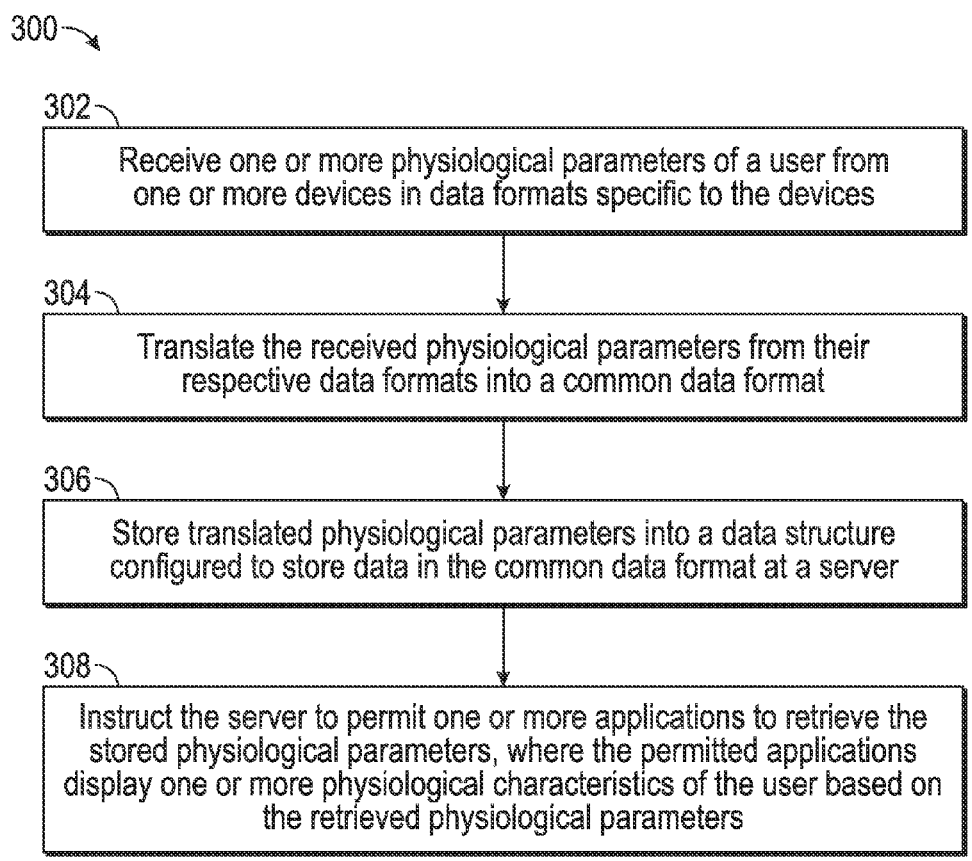

FIG. 3 illustrates another example process 300 for providing physiological characteristics and health-related information at the example client of FIG. 1. While FIG. 3 is described with reference to FIG. 1, it should be noted that the process steps of FIG. 3 may be performed by other systems.

Process 300 begins with receiving one or more physiological parameters of a user from one or more devices in data formats specific to the devices (stage 302). As an example, translator 130 receives one or one or more physiological parameters of a user from devices 170 (e.g., physiological sensors) worn by the user or in proximity to the user. As noted above, devices 170 may be manufactured by the same or different manufacturers and may provide physiological parameters of the user in formats specific to the devices. For example, a heart sensor may provide heart rate parameters in a first data format and a body temperature sensor may provide temperature parameters in a second data format distinct from the first data format.

Process 300 proceeds by translating the received physiological parameters from their respective data formats into a common data format (stage 304). As an example, the physiological parameters received from devices 170 in data formats specific to the devices may be translated by translator 130 from their respective data formats into a common data format. The common data format may, for example, be distinct from the respective data formats. The common data format may be distinct from the respective data formats. In some implementations the common data format may be defined using a mark-up language. The mark-up language may include tags or identifiers to describe a type of physiological parameter, an identifier identifying a device of devices 170 that captured or measured the parameter and a date or time at which the parameter was captured or measured.

The translated physiological parameters are stored in the common data format at a server (stage 308). As an example, the translated physiological parameters may be stored by translator 130 in the common data format at data structure 164 resident at server 190. Server 190 may be configured to store physiological parameters and other health related information in association with one or more user accounts 162A-N. For example, the physiological parameters may be stored in association with a user account 162A of the user accounts 162A-N.

Process 300 proceeds by instructing the server to permit one or more applications to retrieve the stored physiological parameters, where the permitted applications display one or more physiological characteristics of the user based on the retrieved physiological parameters (step 310). As an example, server 190 may be instructed by health application 110 to permit the one or more applications of applications 120A-N to retrieve data from data structure 164 based on an indication from a user of health application 110. For example, the indication from the user may include a selection of user interface elements representing one or more applications 120A-N in health application 110.

When the indication from the user transmitted by health application 110 and is received at server 190, permission engine 160 may store the indication (or permissions) in association with a user account 162A at server 190. When the user opens or executes one or more applications 120A-N, the applications 120A-N may provide a request for the user's physiological parameters stored at data structure 164. Responsive to the request, permission engine 160 may check if the requesting applications have been permitted or authorized via the user's account 162A in the indication. If the requesting applications have been permitted or authorized by via the user's account 162 in the indication, the requesting applications are allowed to retrieve one or more physiological characteristics of the user from data structure 164. Otherwise, permission engine 160 may not allow the requesting applications to access or read data structure 164. The permitted requesting applications may display one or more physiological characteristics of the user based on the retrieved physiological parameters. The physiological characteristics may include physiological parameter values, graphs, imagery, video/animations, and health-related suggestions to the user.

Figure 4:
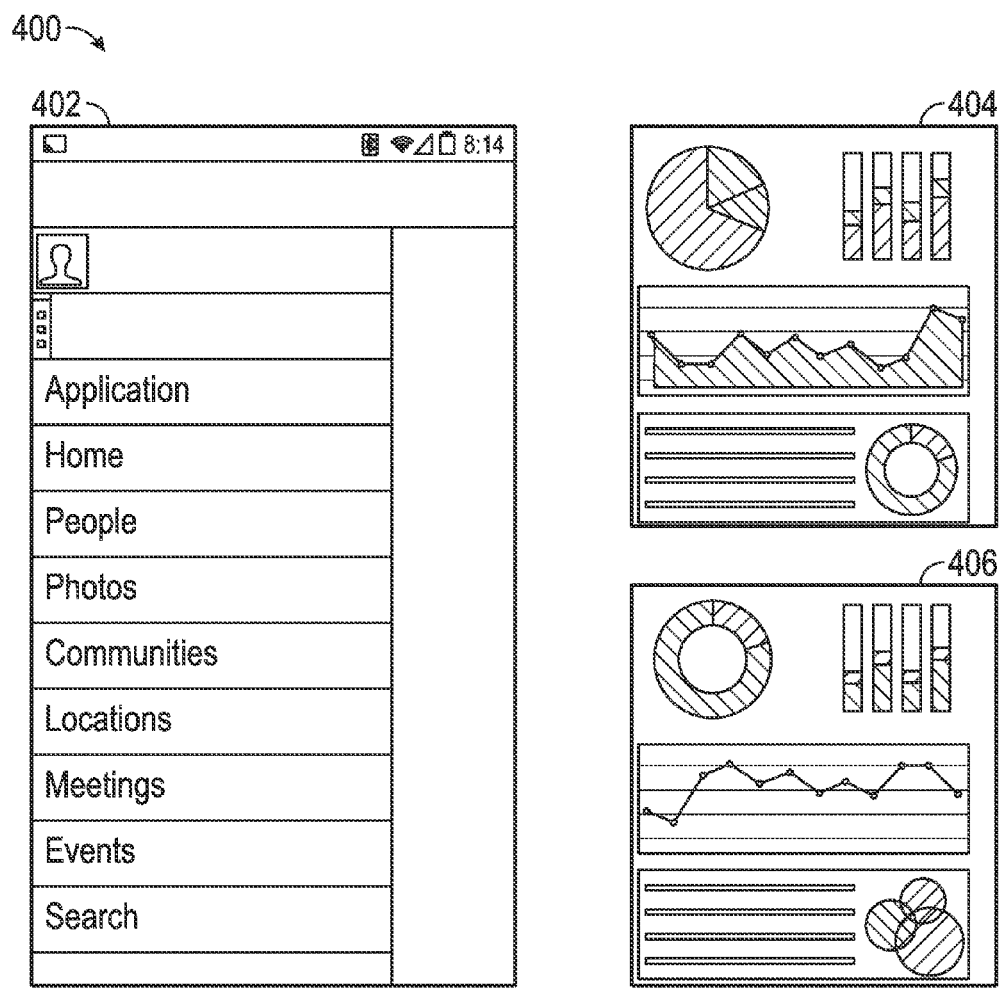
FIG. 4 illustrates example user interfaces in accordance with some implementations of the subject technology.

FIG. 4 illustrates an example user interface and displayed physiological characteristics in accordance with some implementations. User interface 402 illustrates an example home screen 400 that includes a button 402 to instantiate health application 110. Health application 110 may display one or more physiological characteristics including charts and graphs of a user's physiological parameters retrieved from data structure 164. Diagrams 404 and 406 illustrate example visualizations of physiological characteristics that may be presented by health application 110.

Figure 5:
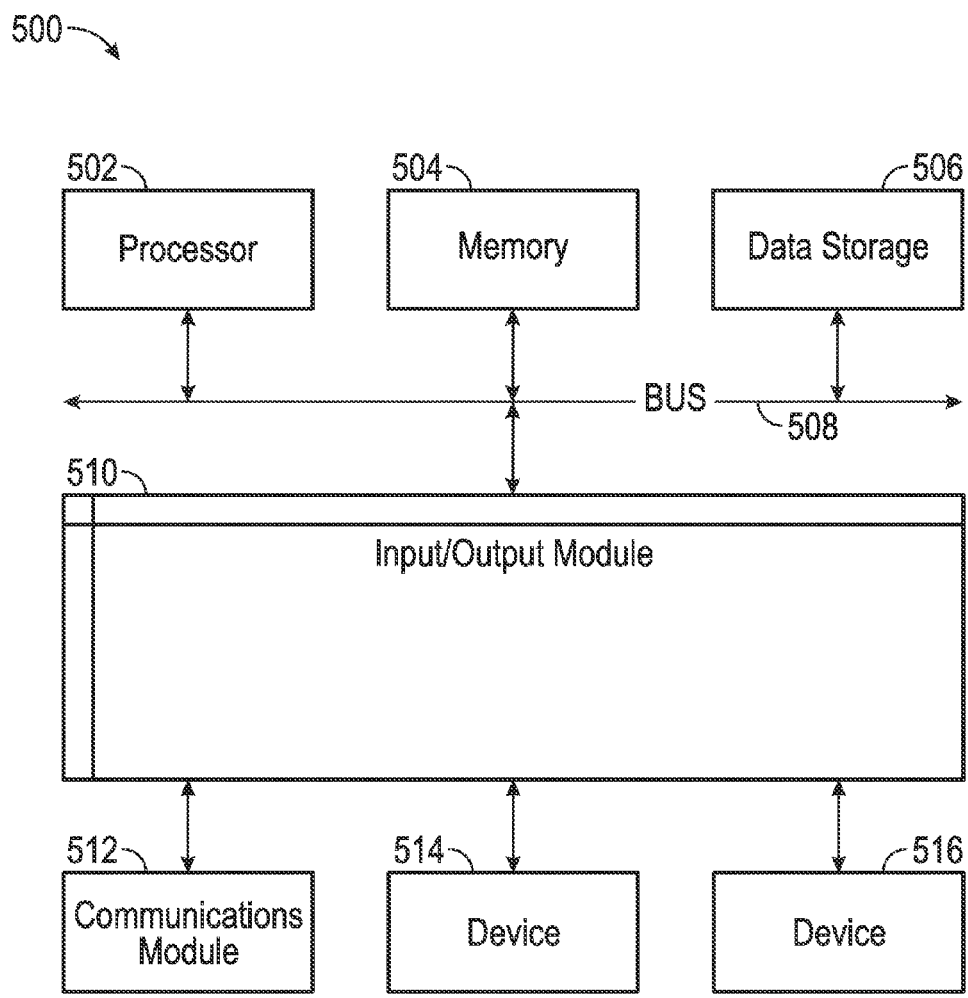
FIG. 5 conceptually illustrates an example electronic system with which some implementations of the subject technology can be implemented.

FIG. 5 is a block diagram illustrating an example computer system 500 with which client 180 and server 190 of FIG. 1 can be implemented. In certain aspects, the computer system 500 may be implemented using hardware or a combination of software and hardware, either in a dedicated server, or integrated into another entity, or distributed across multiple entities.

Computer system 500 (e.g., client 180 and server 190) includes a bus 508 or other communication mechanism for communicating information, and a processor 502 (e.g., processor 212 and 232) coupled with bus 508 for processing information. By way of example, the computer system 500 may be implemented with one or more processors 502. Processor 502 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

Computer system 500 can include, in addition to hardware, code that creates an execution environment for the computer program in question, e.g., code that constitutes processor firmware, a protocol stack, a database management system, an operating system, or a combination of one or more of them stored in an included memory 504 (e.g., memory 220 and 250), such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 508 for storing information and instructions to be executed by processor 502. Processor 502 and memory 504 can be supplemented by, or incorporated in, special purpose logic circuitry.

The instructions may be stored in memory 504 and implemented in one or more computer program products, i.e., one or more modules of computer program instructions encoded on a computer readable medium for execution by, or to control the operation of, the computer system 500, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, embeddable languages, and xml-based languages. Memory 504 may also be used for storing temporary variable or other intermediate information during execution of instructions to be executed by processor 502.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 500 further includes a data storage device 506 such as a magnetic disk or optical disk, coupled to bus 508 for storing information and instructions. Computer system 500 may be coupled via input/output module 510 to various devices. The input/output module 510 can be any input/output module. Example input/output modules 510 include data ports such as USB ports. The input/output module 510 is configured to connect to a communications module 512. Example communications modules 512 (e.g., communications module 118) include networking interface cards, such as Ethernet cards and modems. In certain aspects, the input/output module 510 is configured to connect to a plurality of devices, such as an input device 514 (e.g., input device 119) or an output device 516 (e.g., output device 117). Example input devices 514 include a keyboard and a pointing device, e.g., a mouse or a trackball, by which a user can provide input to the computer system 500. Other kinds of input devices 514 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Example output devices 516 include display devices, such as a LED (light emitting diode), CRT (cathode ray tube), or LCD (liquid crystal display) screen, for displaying information to the user.

According to one aspect of the present disclosure, client 180 and server 190 can be implemented using a computer system 500 in response to processor 502 executing one or more sequences of one or more instructions contained in memory 504. Such instructions may be read into memory 504 from another machine-readable medium, such as data storage device 506. Execution of the sequences of instructions contained in main memory 504 causes processor 502 to perform the process steps described herein. One or more processors in a multi-processing arrangement may also be employed to execute the sequences of instructions contained in memory 504. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. The communication network (e.g., network 150) can include, for example, any one or more of a personal area network (PAN), a local area network (LAN), a campus area network (CAN), a metropolitan area network (MAN), a wide area network (WAN), a broadband network (BBN), the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computing system 500 can include clients and servers. A client and server are generally remote from each other and typically interact through a communication network. The relationship of client and server arises by virtue of computer programs running on the respective computers and having a client-server relationship to each other. Computer system 500 can be, for example, and without limitation, a desktop computer, laptop computer, or tablet computer. Computer system 500 can also be embedded in another device, for example, and without limitation, a mobile telephone, a personal digital assistant (PDA), a mobile audio player, a Global Positioning System (GPS) receiver, a video game console, or a television set top box.

The term "machine-readable storage medium" or "computer readable medium" as used herein refers to any medium or media that participates in providing instructions or data to processor 502 for execution. Such a medium may take many forms, including, but not limited to, non-volatile media, volatile media, and transmission media. Non-volatile media include, for example, optical disks, magnetic disks, or flash memory, such as data storage device 506. Volatile media include dynamic memory, such as memory 504. Transmission media include coaxial cables, copper wire, and fiber optics, including the wires that comprise bus 508. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, or at least one of any combination of the items, or at least one of each of the items. By way of example, the phrases "at least one of A, B, and C" or "at least one of A, B, or C" each refer to only A, only B, or only C; any combination of A, B, and C; or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim.

A reference to an element in the singular is not intended to mean "one and only one" unless specifically stated, but rather "one or more." All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The subject matter of this specification has been described in terms of particular aspects, but other aspects can be implemented and are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other variations are within the scope of the following claims.

These and other implementations are within the scope of the following claims.

What is claimed is:

1. A computer-implemented method comprising:
   electronically receiving, from each of a plurality of devices, one or more physiological parameters of a user, wherein the one or more physiological parameters received from each device is in a data format specific to the device;
   translating, using one or more processors, each of the physiological parameters received from the plurality of devices from their respective data formats into a common data format distinctive from the respective data formats specific to the plurality of devices;
   storing, at a server in association with a user account, the translated physiological parameters in a data structure of the common data format so that the physiological parameters received from the plurality of devices are retrievable in the common data format from the data structure at the server when authorized by the user account;
   electronically receiving a first authorization for a first user contact account to receive a first physiological parameter of the translated physiological parameters and a first time period for the first authorization, and a second authorization for a second user contact account to receive a second physiological parameter of the translated physiological parameters and a second time period for the second authorization, the first and second physiological parameters originating from different devices;
   verifying, using the one or more processors, permissions to retrieve the first physiological parameter for the first user contact account and to retrieve the second physiological parameter for the second user contact account based on the received first authorization and the second authorization; and
   instructing, based on the permissions, the server to permit the first user contact account to retrieve the first physiological parameter for the first time period and the second user contact account to retrieve the second physiological parameter for the second time period, wherein one or more applications display one or more physiological characteristics of the user based on the retrieved physiological parameters.

2. The computer-implemented method of claim 1, further comprising:
   retrieving the translated physiological parameters from the server; and
   displaying the retrieved physiological parameters to the user in association with a user's account at the server.

3. The computer-implemented method of claim 2, further comprising:
   correlating the stored physiological parameters to predetermined physiological characteristics based on physiological parameters of one or more other users; and
   displaying a result of the correlation to the user.

4. The computer-implemented method of claim 2, further comprising:
   comparing the retrieved physiological parameters of the user to translated physiological parameters of another user identified by the user; and
   displaying a result of the comparison to the user.

5. The computer-implemented method of claim 1, further comprising:
   receiving an indication to share the stored physiological parameters with the one or more applications, wherein the one or more applications are permitted to retrieve the stored physiological parameters is based on the indication.

6. The computer-implemented method of claim 1, further comprising:
   receiving an indication to share the stored physiological parameters for a time range, wherein the one or more applications are permitted to retrieve the stored physiological parameters is based on the indication.

7. The computer-implemented method of claim 1, further comprising:
   receiving an indication to share the translated physiological parameters with one or more social networks, wherein the one or more applications are permitted to retrieve the stored physiological parameters is based on the indication.

8. The computer-implemented method of claim 1, wherein the one or more physiological parameters received from each device is in a data format different from a data format of physiological parameters received from other of the plurality of devices, and wherein the storing further comprises:
   storing one or more identifiers with the translated physiological parameters, the identifiers identifying at least one of a type of parameter, a time at which the parameter was received, and a device that measured the parameter.

9. A non-transitory machine-readable medium comprising instructions stored therein, which when executed by a processor, causes the processor to perform operations comprising:
   electronically receiving, from each of a plurality of devices, one or more physiological parameters of a user, wherein the one or more physiological parameters received from each device is received in real time in a data format specific to the device;
   translating, using one or more processors, each of the physiological parameters in real time when received from the plurality of devices from their respective data formats into a data structure of a common data format distinctive from the respective data formats specific to the plurality of devices;

storing, at a server in association with a user account, the translated physiological parameters into a common data structure configured to store data in the common data format, the physiological parameters received from the plurality of devices being retrievable in the common data format and in real time from the data structure when authorized by the user account;

electronically retrieving the stored physiological parameters for display in a user interface, wherein the user interface displays one or more human-readable physiological characteristics of the user based on the retrieved physiological parameters and a result of correlation;

electronically receiving a first authorization for a first user contact account to receive a first physiological parameter of the translated physiological parameters and a first time period for the first authorization, and a second authorization for a second user contact account to receive a second physiological parameter of the translated physiological parameters and a second time period for the second authorization, the first and second physiological parameters originating from different devices;

verifying, using the one or more processors, permissions to retrieve the first physiological parameter for the first user contact account and to retrieve the second physiological parameter for the second user contact account based on the received first authorization and the second authorization;

instructing, based on the permissions, the server to permit the first user contact account to retrieve the first physiological parameter for the first time period, and the second user contact account to retrieve the second physiological parameter for the second time period; and repeating the translating, the storing and the retrieving, upon receipt of one or more other physiological parameters from the plurality of devices, to update the displayed human-readable physiological characteristics.

10. The machine-readable medium of claim 9, wherein the translating comprises:

generating a file in the common data format, the file configured to store the translated physiological parameters, the file including one or more identification tags identifying a value of a physiological parameter, a type of parameter, a time at which the parameter was measured and a device that measured the parameter.

11. The machine-readable medium of claim 9, further comprising:

correlating the stored physiological parameters to predetermined physiological characteristics based on physiological parameters of one or more other users; and displaying a result of the correlation to the user.

12. The machine-readable medium of claim 9, further comprising:

comparing the retrieved physiological parameters of the user to translated physiological parameters of another user identified by the user; and displaying a result of the comparison to the user.

13. The machine-readable medium of claim 9, further comprising:

receiving an indication to share the stored physiological parameters with applications; and based on the indication, instructing the server to provide access to the stored physiological parameters by the applications.

14. The machine-readable medium of claim 13, further comprising:

receiving an indication to share the stored physiological parameters for a time range; and based on the indication, instructing the server to provide the access to the shared physiological parameters for the time range.

15. The machine-readable medium of claim 13, further comprising:

receiving an indication to share the translated physiological parameters with one or more social media networks; and based on the indication, instructing the server to provide the access to the shared physiological parameters to the social media networks.

16. A system comprising: a memory comprising instructions; and a processor configured to execute the instructions to:

electronically receive, from each of a plurality of devices, one or more physiological parameters of a user, wherein the one or more physiological parameters received from each device is received in real time in a data format specific to the device;

translate, using one or more processors, each of the physiological parameters in real time when received from the plurality of devices from their respective data formats into a common data format distinctive from the respective data formats specific to the plurality of devices;

store, at a server in association with a user account, the translated physiological parameters in a data structure of the common data format so that the physiological parameters received from the plurality of devices are retrievable in the common data format in real time from the data structure at the server when authorized by the user account;

electronically receiving a first authorization for a first user contact account to receive a first physiological parameter of the translated physiological parameters and a first time period for the first authorization, and a second authorization for a second user contact account to receive a second physiological parameter of the translated physiological parameters and a second time period for the second authorization, the first and second physiological parameters originating from different devices;

verify permissions to retrieve the first physiological parameter for the first user contact account and to retrieve the second physiological parameter for the second user contact account based on the received first authorization and the second authorization; and instruct, based on the permissions, the server to permit the first user contact account to retrieve the first physiological parameter for the first time period and the second user contact account to retrieve the second physiological parameter for the second time period, wherein one or more applications display one or more physiological characteristics of the user based on the retrieved physiological parameters.

17. The system of claim 16, wherein the processor is further configured to execute the instructions to:

retrieve the translated physiological parameters from the server; and display the retrieved physiological parameters to the user in connection with an authorization associated with the user account at the server.

18. The system of claim 17, wherein the processor is further configured to execute the instructions to:
   correlate the stored physiological parameters to pre-determined physiological characteristics based on physiological parameters of one or more other users; and
   display a result of the correlation to the user.

19. The system of claim 17, wherein the processor is further configured to execute the instructions to:
   compare the retrieved physiological parameters of the user to translated physiological parameters of another user identified by the user; and
   display a result of the comparison to the user.

20. The system of claim 16, wherein the processor is further configured to execute the instructions to:
   receive an indication to share the stored physiological parameters with the applications, wherein the server is instructed to permit the applications to retrieve the stored physiological parameters is based on the indication.

\* \* \* \* \*